US005730972A

United States Patent [19]

Simon et al.

[11] Patent Number: 5,730,972
[45] Date of Patent: Mar. 24, 1998

[54] COMPOSITION FOR COMBATING SKIN MARKS AND/OR AGEING OF THE SKIN AND USES THEREOF

[75] Inventors: Pascal Simon, Vitry sur Seine; Didier Candau, Bievres, both of France

[73] Assignee: L'Oreal, Paris, France

[21] Appl. No.: 635,672

[22] Filed: Apr. 22, 1996

[30] Foreign Application Priority Data

Apr. 20, 1995 [FR] France ................................. 95 04748

[51] Int. Cl.$^6$ ........................... A61K 7/42; A61K 7/44; A61K 7/00
[52] U.S. Cl. ........................... 424/59; 424/60; 424/400; 424/401
[58] Field of Search ........................... 424/59, 60, 400, 424/401

[56] References Cited

FOREIGN PATENT DOCUMENTS

| 0 398 484 | 11/1990 | European Pat. Off. . |
| 0 425 066 | 5/1991 | European Pat. Off. . |
| 0 457 687 | 11/1991 | European Pat. Off. . |
| 0 487 404 | 5/1992 | European Pat. Off. . |
| 0 518 772 | 12/1992 | European Pat. Off. . |
| 0 531 192 | 3/1993 | European Pat. Off. . |
| 59-27825 | 2/1984 | Japan . |
| 62-33195 | 2/1987 | Japan . |
| 5-213736 | 8/1993 | Japan . |
| 2 200 552 | 8/1988 | United Kingdom . |
| 2 225 013 | 5/1990 | United Kingdom . |

OTHER PUBLICATIONS

Patent Abstracts of Japan No. 62–33195, vol. 11, No. 214, (C–434),(2661), Jul. 10, 1987 (Japanese Reference Also Provided).

Patent Abstracts of Japan No. 57–138821, vol. 8, No. 114, (C–225), (1551), May 26, 1984 (Japanese Reference Also Provided).

Database WPI, Week 9338, Aug. 24, 1993, Derwent Publications Ltd., London, GB, AN 93–299537 (Japanese Reference Also Provided).

*Primary Examiner*—Shelley A. Dodson
*Attorney, Agent, or Firm*—Oblon, Spivak, McClelland, Maier & Neustadt, P.C.

[57] ABSTRACT

The invention relates to a composition for combating skin marks and/or ageing of the skin, containing, in a cosmetically and/or dermatologically acceptable medium, at least one saccharide ester of ascorbic acid and a water-soluble sulphonic UVA screening agent.

20 Claims, No Drawings

COMPOSITION FOR COMBATING SKIN MARKS AND/OR AGEING OF THE SKIN AND USES THEREOF

BACKGROUND OF THE INVENTION

1. Field of the Invention

The invention relates to a cosmetic and/or dermatological composition intended to prevent and/or combat skin marks and/or ageing of the skin. This composition is in the form of a smooth white cream which may be applied to the human face, body, neck, hands and/or legs.

The invention also relates to a use of this composition for the cosmetic treatment of the skin, to the use of this composition for the preparation of a cream intended for the dermatological treatment of the skin and to a cosmetic treatment process.

2. Description of the Background

During the process of ageing, various signs appear on the skin which are very characteristic of this ageing, this being reflected in particular in a modification of the structure and functions of the skin. This ageing is physiological in nature but may also be photoinduced, that is to say due to the repeated exposure of the skin to sunlight, in particular ultraviolet light. The action of this light on the constituents of the skin and on the sebum secreted by the skin leads in particular to the formation of oxygen-containing free radicals. Now, these radicals cause considerable damage, in particular in cell membranes (permeability of the membranes), in cell nuclei (mutation by action on RNA or DNA) and in tissues (necroses, degeneration); it is thus necessary to protect the skin against these free radicals.

The main clinical signs of ageing of the skin are, in particular, the appearance of fine lines and deep wrinkles, which increase with age, as well as a disorganization of the "grain" of the skin; in other words, the skin microrelief is less uniform and is anisotropic in nature.

Moreover, the skin complexion is generally modified and appears yellower; this appears to be due essentially to a disorganization of the microcirculation (less haemoglobin in the papillary dermis). Furthermore, many coloured and/or darker marks appear at the surface of the skin, and in particular on the hands, imparting non-uniformity to the skin. In general, these marks are due to an appreciable production of melanin in the skin epidermis and/or dermis. In certain cases of intense exposure to solar rays, these marks may become cancerous. Moreover, diffuse irritations and occasionally telangiectasias may exist on certain areas of the skin.

Another clinical sign of ageing is the dry and coarse appearance of the skin, which is due essentially to a more pronounced desquamation; by diffracting light rays, these squama also contribute towards the somewhat greyish appearance of the complexion.

Lastly, a loss of firmness and tonicity of the skin is observed which, as for wrinkles and fine lines, is at least partly explained by dermal and epidermal atrophy as well as by a flattening out of the dermoepidermal formation; the skin is thinner and more flaccid and the thickness of the epidermis decreases.

It is thus observed that the clinical signs of ageing of the skin result essentially from dysfunction of the main biological mechanisms involved in the skin.

SUMMARY OF THE INVENTION

Thus, the composition according to the invention is a composition capable of preventing and/or combating the onset of ageing and the existing signs of ageing, such as wrinkles and fine lines, which is capable of preventing and/or combating skin pigmentation marks, irrespective of their origin, and which is capable of protecting the skin in particular by suppression of the formation of oxygen-containing free radicals.

One of the means known for combating premature ageing of the skin consists in supplying the skin with molecules capable of aiding the cells to defend themselves against the excess of photoinduced free radicals. One of the effective means of combating these free radicals is the use of a screening agent which absorbs UVA radiation (320 nm to 400 nm). This screening agent may be lipophilic or hydrophilic.

For the purpose of manufacturing a large variety of stable compositions for topical use, the invention is concerned with hydrophilic or water-soluble screening agents, lipophilic or liposoluble screening agents limiting the use of excipients.

Water-soluble screening agents absorbing UVA radiation which are known are Uvinul MS-40 from BASF, which is 2-hydroxy-4-methoxy-5-benzophenonesulphonic acid, and sulphonic derivatives of benzylidenecamphor such as benzene-1,4-[di(3-methylidene-10-camphorsulphonic)] acid, also known (according to the CTFA nomenclature—5th edition) as terephthalylidene-di-camphorsulphonic acid.

For more effective control against free radicals, it is advantageous to combine the OVA screening agents with molecules capable of blocking the chain reactions of free radicals before the final steps of degradation of the biological constituents of the skin (lipids, proteins and nucleic acids). These molecules are, in particular, antioxidants and/or anti-free-radical agents.

One of the molecules known to have a powerful hydrophilic reducing power and known to react with free radicals such as peroxide, superoxide and hydroxyl radicals is vitamin C. Unfortunately, this vitamin is very unstable in aqueous medium and thus cannot be combined with the abovementioned water-soluble sulphonic screening agents.

The object of the invention is, precisely, a composition for topical application which has a high protective power against photoinduced radicals, making it possible to effectively prevent and/or combat ageing of the skin and/or extrinsic and intrinsic (physiological) skin marks, this composition capable of being in various pharmaceutical forms.

According to an essential characteristic of the invention, this composition contains, in a cosmetically and/or dermatologically acceptable medium, at least one saccharide ester of ascorbic acid and at least one water-soluble sulphonic UVA screening agent.

Thus, the Applicant has discovered, surprisingly, that the saccharide derivatives of ascorbic acid were entirely compatible with water-soluble sulphonic UVA screening agents and that they could be formulated in any type of excipient containing water. These derivatives have the advantage in particular of being very water-soluble and of not modifying the physical and chemical properties of these screening agents. Furthermore, these derivatives are bioconvertible into vitamin C by corresponding skin enzymes.

DESCRIPTION OF THE PREFERRED EMBODIMENTS

The composition of the invention may advantageously be in any pharmaceutical form normally used for topical application, such as solutions, aqueous or aqueous-alcoholic gels, oil-in-water or water-in-oil emulsions, and more particularly droplets of oil dispersed by spherules in an aqueous phase. These spherules may be polymer nanoparticles such as nanospheres and nanocapsules or, better still, lipid vesicles. Thus, the composition of the invention may be in the form of a cream, an ointment, a lotion or a serum.

The composition makes it possible to attenuate wrinkles and fine lines effectively, to modify the complexion of the skin, which appears rosier, to remove pigmentation marks, to eliminate squama and to give the skin a more elastic consistency. It allows effective protection of the skin against solar rays as well as bleaching of the skin.

The saccharide esters of ascorbic acid which may be used in the invention are, in particular, the glycosyl, mannosyl, fructosyl, fucosyl, galactosyl, N-acetylglucosamine and N-acetylmuramic derivatives of ascorbic acid and mixtures thereof and, more especially, ascorbyl-2-glucoside or 2-O-α-D-glucopyranosyl L-ascorbate or alternatively 6-O-β-D-galactopyranosyl L-ascorbate. The latter compounds and their methods of manufacture are described in particular in the documents EP-A-487,404, EP-A-425,066 and J05213736.

The UVA screening agents which may be used in the invention are any water-soluble sulphone-containing and/or sulphonate-containing screening agents. These screening agents may be partially neutralized with an organic base such as triethanolamine or ethylenediamine.

The screening agents of the invention are advantageously sulphone-containing or sulphonate-containing derivatives of benzylidenecamphor, but sulphone-containing or sulphonate-containing benzophenone derivatives may also be used.

In particular, the benzylidenecamphor derivatives which may be used in the invention have the following general formula (a):

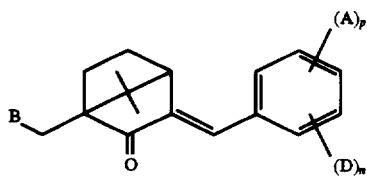

in which:

B represents —H or —SO₃H,

0≦n≦1 with B=—SO₃H when p=0, 0≦n≦4,

D represents one or more linear or branched alkyl or alkoxy radicals, which may be identical or different when n≧2, containing from 1 to 18 carbon atoms approximately, a halo radical or a hydroxyl radical.

A, preferably in the meta or para position, represents either an SO₃H radical;

or a group:

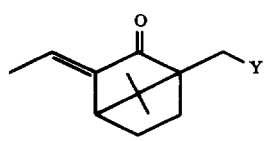

in which Y represents H or SO₃H;

or a group:

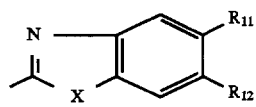

in which:

$R_{11}$ denotes a hydrogen atom, a linear or branched alkyl or alkoxy radical containing from 1 to 6 carbon atoms approximately or the —SO₃H radical, $R_{11}$ being —SO₃H when B=—H, $R_{12}$ denotes a hydrogen atom or a linear or branched alkyl or alkoxy radical containing from 1 to 6 carbon atoms approximately, X is an oxygen or sulphur atom or a group —NR—, R being a hydrogen atom or a linear or branched alkyl radical containing from 1 to 6 carbon atoms approximately, and in which at least one —SO₃H function is optionally neutralized.

Specific examples of compounds of formula (a) are the derivatives of formulae (I), (II) and (III) below:

Formula (I):

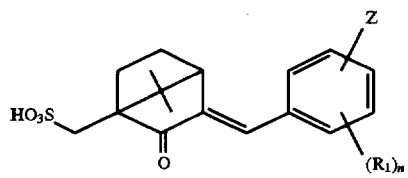

in which:

Z, preferably in the para or meta position, denotes a group

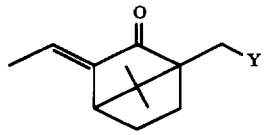

in which Y represents —H or —SO₃H, optionally neutralized, n is equal to 0 or is a number ranging from 1 to 4 (0≦n≦4), $R_1$ represents one or more linear or branched alkyl or alkoxy radicals, which may be identical or different, containing from 1 to 4 carbon atoms approximately.

A particularly preferred compound of formula (I) is that corresponding to n=0, Z in the para position and Y=—SO₃H: benzene-1,4-[di(3-methylidene-10-camphorsulphonic)] acid, also known (according to the CTFA nomenclature—5th edition) as terephthalylidene-di-camphorsulphonic acid.

Formula (II):

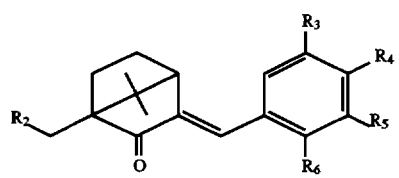

in which:

$R_2$ denotes a hydrogen atom or an —SO₃H radical, $R_3$, $R_4$, $R_5$ and $R_6$, which may be identical or different, represent a hydroxyl group, a linear or branched alkyl radical having from 1 to 4 carbon atoms approximately, a linear or branched alkenyl radical having from 2 to 4 carbon atoms approximately, a linear or branched alkoxy radical having from 1 to 4 carbon atoms, a linear or branched alkenyloxy radical having from 2 to 4 carbon atoms, or a halo radical, furthermore, only one radical $R_3$ to $R_6$ may be an —$SO_3H$ radical, at least one of the radicals $R_3$ to $R_6$ denoting the —$SO_3H$ radical when $R_2$ is a hydrogen atom. One or more —$SO_3H$ functions may also be neutralized.

Specific examples are the following compounds of formula (II) in which:

$R_4$ denotes the —$SO_3H$ radical in the para position of benzylidenecamphor and $R_2$, $R_3$, $R_5$ and $R_6$ each denote a hydrogen atom, that is to say 3-benzylidenecamphor-4'-sulphonic acid.

$R_3$, $R_4$, $R_5$ and $R_6$ each denote a hydrogen atom and $R_2$ denotes an —$SO_3H$ radical, that is to say 3-benzylidene-10-camphorsulphonic acid.

$R_4$ denotes a methyl radical in the para position of benzylidenecamphor, $R_5$ is an —$SO_3H$ radical and $R_2$, $R_3$ and $R_6$ represent a hydrogen atom, that is to say 3-benzylidenecamphor-4'-methyl -3'-sulphonic acid.

$R_4$ denotes a chlorine atom in the para position of benzylidenecamphor, $R_5$ is an —$SO_3H$ radical and $R_2$, $R_3$ and $R_6$ represent a hydrogen atom, that is to say 3-benzylidenecamphor-4'-chloro-3'-sulphonic acid.

$R_4$ denotes a methyl radical in the para position of benzylidenecamphor, $R_3$, $R_5$ and $R_6$ denote a hydrogen atom and $R_2$ denotes an —$SO_3H$ radical, that is to say 4'-methyl-3-benzylidene-10-camphorsulphonic acid.

$R_2$ represents an —$SO_3H$ radical, $R_3$ is a methyl radical, $R_4$ is a hydrogen atom, $R_5$ is a tert-butyl radical and $R_6$ is a hydroxyl radical, that is to say 3-(3-t-butyl-2-hydroxy-5-methyl)benzylidene-10-camphorsulphonic acid.

$R_2$ represents an —$SO_3H$ radical, $R_3$ is a methoxy radical, $R_4$ is a hydrogen atom, $R_5$ is a tert-butyl radical and $R_6$ is a hydroxyl radical, that is to say 3-(3-t-butyl-2-hydroxy-5-methoxy)benzylidene-10-camphorsulphonic acid.

$R_2$ represents an —$SO_3H$ radical, $R_3$ and $R_5$ each denote a tert-butyl radical, $R_4$ is a hydroxyl radical, and $R_6$ is a hydrogen atom, that is to say 3-(3,5-di-tert-butyl-4-hydroxy)benzylidene-10-samphorsulphonic acid.

$R_4$ represents a para-methoxy radical, $R_5$ represents —$SO_3H$ and the radicals $R_2$, $R_3$ and $R_6$ represent H, that is to say 3-benzylidenecamphor-4'-methoxy-3'-sulphonic acid.

$R_2$ denotes an —$SO_3H$ radical, $R_3$ and $R_6$ represent H, and $R_4$ and $R_5$ form a methylenedioxy radical, that is to say 3-(4,5-methylenedioxy)benzylidene-10-camphorsulphonic acid.

$R_2$ represents an —$SO_3H$ radical, $R_4$ is a methoxy radical and the radicals $R_3$, $R_5$ and $R_6$ represent H, that is to say 3-(4-methoxy)benzylidene-10-camphorsulphonic acid.

$R_2$ represents an —$SO_3H$ radical, $R_4$ and $R_5$ are both a methoxy radical and the radicals $R_3$ and $R_6$ represent H, that is to say 3-(4,5-dimethoxy)benzylidene-10-camphorsulphonic acid.

$R_2$ represents an —$SO_3H$ radical, $R_4$ is an n-butoxy radical and the radicals $R_3$, $R_5$ and $R_6$ represent a hydrogen atom, that is to say 3-(4-n-butoxy)benzylidene-10-camphorsulphonic acid.

$R_2$ represents an —$SO_3H$ radical, $R_4$ is an n-butoxy radical, $R_5$ is a methoxy radical and $R_3$ and $R_6$ both denote a hydrogen atom, that is to say 3-(4-n-butoxy-5-methoxy)benzylidene-10-camphorsulphonic acid.

Formula (III):

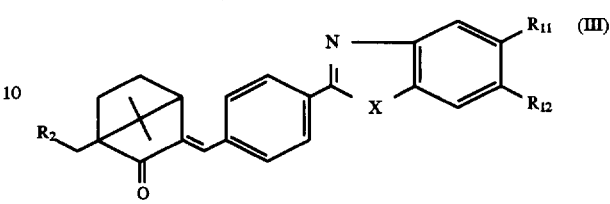

in which:

$R_{11}$ denotes a hydrogen atom, a linear or branched alkyl or alkoxy radical containing from 1 to 6 carbon atoms approximately or an —$SO_3H$ radical, $R_{12}$ denotes a hydrogen atom or a linear or branched alkyl or alkoxy radical containing from 1 to 6 carbon atoms approximately, $R_{13}$ denotes a hydrogen atom or an —$SO_3H$ radical, at least one of the radicals $R_{11}$ and $R_{13}$ denoting an —$SO_3H$ radical, X is an oxygen or sulphur atom or an —NR— group, R being a hydrogen atom or a linear or branched alkyl radical containing from 1 to 6 carbon atoms approximately.

A specific example of a compound of formula (III): the compound in which X denotes an —NH— radical, $R_{11}$ denotes an —$SO_3H$ radical and $R_{12}$ and $R_{13}$ both denote a hydrogen atom, that is to say 2-[4-(camphormethylidene)phenyl]benzimidazole-5-sulphonic acid.

The compounds of structures (I), (II) and (III) are described in U.S. Pat. No. 4,585,597 and patents FR 2,236, 515, 2,282,426, 2,645,148, 2,430,938 and 2,592,380.

Other examples of benzylidenecamphor derivatives which may be used in the invention are compounds of the following general formula (b):

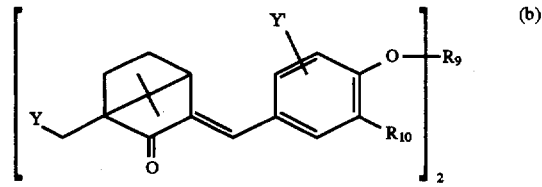

in which:

$R_9$ denotes a divalent radical: —$(CH_2)_m$— or —$CH_2$—CHOH—$CH_2$—, m being an integer ranging from 1 to 10 ($1 \leq m \leq 10$), $R_{10}$ denotes a hydrogen atom, an alkoxy radical containing from 1 to 4 carbon atoms approximately or a divalent radical —O— connected to the radical $R_9$ when this is also divalent, Y and Y' denote a hydrogen atom or an —$SO_3H$ radical, at least one of these radicals Y or Y' being other than hydrogen. Here also, the —$SO_3H$ function may be neutralized.

Specific examples are the following compounds of formula (b) in which Y represents —$SO_3H$, Y' is —H, $R_{10}$ is H and $R_9$ is —$CH_2$—$CH_2$—, that is to say ethylenebis [3-(4'-oxybenzylidene)-10-camphorsulphonic]acid.

According to the invention, the amount of saccharide derivatives of ascorbic acid is chosen, for example, from 0.05% to 20% by weight relative to the total weight of the composition and preferably from 0.5% to 10% and, better still, from 0.5% to 5%. Furthermore, the composition may contain one or more saccharide derivatives.

Similarly, the amount of UVA screening agent which may be used in the invention is that generally used in the fields concerned. In practice, from 0.1% to 10% by weight are used relative to the total weight of the composition and preferably from 0.1% to 5%. Furthermore, the composition may contain one or more water-soluble UVA screening agents.

The oils which may be used in the invention are those generally used in the fields concerned. They may be plant, mineral or synthetic oils and optionally silicone-containing and/or fluoro oils.

The invention may also contain hydrophilic or lipophilic adjuvants such as gelling agents, preserving agents, opacifiers, emulsifiers, co-emulsifiers, fragrances and solubilizing or peptizing agents thereof, dyes, pigments, fillers and lipophilic or hydrophilic active agents other than the saccharide ester of ascorbic acid and the UVA screening agent.

The amounts of oil and water are generally those used in the fields considered and depend on the pharmaceutical form of the composition. For an oil-in-water emulsion or a dispersion of oil in water by lipid spherules, the oil may represent from 2% to 40% by weight relative to the total weight of the composition.

Similarly, the adjuvants are used in the usual mount and may represent, in total, from 0.1% to 20% by weight. Their amount depends on their nature.

The composition of the invention may be applied topically to any part of the body or face.

An object of the invention is also the use of the composition defined above for the cosmetic treatment of wrinkles and/or fine lines on the skin as well as the use of this composition for toning, moisturizing and/or firming up the skin.

An object of the invention is also the use of the composition defined above for the cosmetic treatment of skin marks due to ageing, these marks being on the face and/or the body, including the hands and the scalp, as well as for the preparation of a cream intended for the treatment of skin marks of pathological origin.

An object of the invention is also a process for the cosmetic treatment of the skin, which consists in applying the composition defined above to the skin.

The following tests demonstrated the advantages of the present invention. The aim of the tests was to show the ability of the compositions of the invention to effectively attenuate wrinkles and fine lines, modify the skin complexion, which appears rosier, remove pigmentation marks, eliminate squama and give the skin a more elastic consistency. It allows effective protection of the skin against solar rays as well as bleaching of the skin.

The tests were carried out on an expert panel composed of 15 individuals. The cream was applied for several days at a rate of one application per day. The panel members gave their response to the following criteria: healthier appearance, less ashen complexion and smoother skin. The results are as follows:

9 out of the 15 people experienced a very pronounced, pronounced or moderately pronounced effect regarding the sensation of having a healthier appearance, the sensation of having a less ashen complexion and the sensation of having a smoother skin.

Other characteristics and advantages of the invention will emerge more clearly from the description which follows, and which is given by way of illustration and with no limitation being implied. In the examples below of cosmetic and/or dermatological compositions in accordance with the invention, the compositions are given as % by weight.

EXAMPLE 1

Oil-in-water cream for the prevention of skin pigmentation

| | Composition | |
|---|---|---|
| $A_1$ | Sorbitan tristearate (emulsifying agent) | 0.7% |
| | Polyethylene glycol stearate (40 EO) (emulsifying agent) | 1.6% |
| | Cetyl alcohol (co-emulsifying agent) | 3.2% |
| | Glyceryl mono-, di- and tripalmitostearate (emulsifying agent) | 2.4% |
| | Myristyl myristate (oil) | 2% |
| | Liquid fraction of karite butter (oil) | 2% |
| | Preserving agent | 0.2% |
| $A_2$ | Cyclopentadimethylsiloxane (oil) | 15% |
| B | Demineralized water qs | 100% |
| | Glycerol (moisturizing agent) | 3% |
| | Ascorbyl-2-glucoside sold by Hayashibara | 1% |
| | Preserving agent | 0.2% |
| C | 33% Terephthalylidene-di-camphorsulphonic acid in water | 2% |
| | Triethanolamine (neutralizing agent) | 0.3% |
| D | Fragrance | 0.3% |

Preparation of phase $A_1+A_2$

The constituents of $A_1$ are solubilized at 80° C. When the mixture is clear, the temperature is lowered to 65° C. and $A_2$ is added. The mixture should become clear and uniform. The temperature of 65° C. is maintained.

Manufacture

The constituents of B are solubilized at 85° C–90° C. in a manufacturing beaker. After checking that the solution is clear, the temperature is cooled to 65° C. The emulsion is prepared, with stirring, by pouring ($A_1+A_2$) into B. Cooling is continued with stirring. At 40° C., phase C is added and stirring is then continued. Lastly, the fragrance is added and the mixture is allowed to cool to 20° C. with stirring.

EXAMPLE 2

Oil-in-water cream for removing marks

| | Composition | | |
|---|---|---|---|
| $A_1$ | Demineralized water | | 10% |
| | Cholesterol | } | 1.5% |
| | Polyethylene glycol | | |
| | monostearate | } (vesicles) | 1.5% |
| | Monosodium salt | | |
| | n-stearic acid of | } | 0.2% |
| | of α-glutamic acid | | |
| $A_2$ | Demineralized water | | 13% |
| | Glycerol (moisturizing agent) | | 3% |
| | Preserving agent | | 0.7% |
| B | Apricot kernel oil | | 9% |
| | Refined soya oil | | 4% |
| | Cyclopentadimethylsiloxane (oil) | | 10% |

-continued

| | Composition | |
|---|---|---|
| | Preserving agent | 0.1% |
| | Fragrance | 0.3% |
| C | Carboxyvinyl polymer synthesized in methylene chloride (gelling agent) | 0.7% |
| | Demineralized water | 36.45% |
| | Triethanolamine (neutralizing agent) | 0.7% |
| D | Demineralized water | 5% |
| | Ascorbyl-2-glucoside | 1% |
| E | 33% Terephthalylidene-di-camphor-sulphonic acid in water | 2.3% |
| | Triethanolamine | 0.6% |

Manufacture

The constituents of $A_1$ are melted at 100° C. They are allowed to swell with stirring for 1 h 30. When the mixture is uniform, $A_2$ is added; the temperature is stabilized at 80° C. The mixture is then passed twice through a high-pressure homogenizer in order to form vesicles.

B is prepared at 70° C.; the mixture should be clear. It is cooled to 50° C. B is added to A at 50° C. The mixture is then passed twice through the high-pressure homogenizer in order to disperse the fatty phase B. It is cooled to 30° C. C is added (the gel will have been prepared beforehand in water at 80° C., by powdering in the carboxyvinyl polymer; after the latter has swollen, it is neutralized with triethanolamine, with stirring; the gel should be quite smooth). D is added, followed by E. Stirring is continued for 5 minutes. The manufacture is complete.

EXAMPLE 3

Gel for protecting against solar rays

| | Composition | |
|---|---|---|
| A | Demineralized water qs | 100% |
| | Glycerol | 3% |
| | Methyl para-hydroxybenzoate | 0.2% |
| | Ascorbyl-2-glucoside | 1% |
| | Xanthan gum (thickener) | 0.2% |
| B | Parsol MCX (UVB screening agent) | 4% |
| | Alkylbenzoate (Finsolv TN, Witco company) | 4% |
| | Alkylated carboxyvinyl polymer (Pemulen TR 2, Goodrich company) | 0.45 % |
| | Triethanolamine | 0.45% |
| C | 33% Terephthalylidene-di-camphor-sulphonic acid in water | 2.3% |
| | Triethanolamine | 0.6% |

Manufacture

Phase A is prepared by powdering the gelling agent into the water containing the dissolved ingredients, with stirring. The mixture is emulsified by incorporating phase B into phase A, with vigorous stirring. The mixture is smoothed out and left to cool, with slow paddle stirring. At 35° C., C is added. The mixture is allowed to cool to 25° C. The manufacture of the gel is complete.

EXAMPLE 4

"Clear complexion" lotion

| | Composition | |
|---|---|---|
| A | Oxyethylenated hydrogenated ricinoleic triglycerides (60 EO) (peptizing agent) | 0.09% |
| | Fragrance | 0.03% |
| B | Demineralized water qs | 100% |
| | Glycerol | 5.5% |
| | Ascorbyl-2-glucoside | 1% |
| | Preserving agent | 0.3% |
| C | 33% Terephthalylidene-di-camphor-sulphonic acid in water | 2.3% |
| | Triethanolamine | 0.6% |

Manufacture

The constituents of A are mixed together at 40° C. When they are fully solubilized, the constituents of B are successively added at room temperature. Stirring is maintained and correct solubilization of the constituents is confirmed. C is added; the mixture should be clear. The manufacture is complete.

The disclosure of French priority application 95-04748, filed Apr. 20, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United State:

1. A composition comprising at least one water-soluble sulphonic UVA screening agent and at least one saccharide ester of ascorbic acid which is compatible with said screening agent, in a cosmetically and/or dermatologically acceptable medium.

2. A composition comprising at least one water-soluble sulphonic UVA screening agent and at least one saccharide ester of ascorbic acid which is compatible with said screening agent, in a cosmetically and/or dermatologically acceptable medium, wherein the screening agent is selected from the group consisting of sulphone-containing or sulphonate-containing benzylidenecamphor derivatives.

3. The composition according to claim 2, wherein the screening agent has the following formula (I):

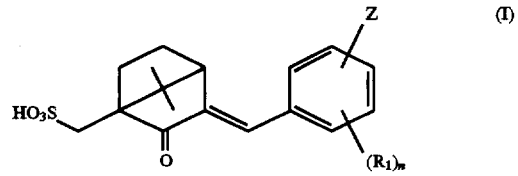

in which:

Z denotes a group

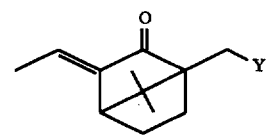

in which Y represents —H or —$SO_3H$, optionally neutralized, n is equal to 0 or is a number ranging from 1 to 4, R₁ represents one or more linear or branched alkyl or alkoxy radicals, which may be identical or different, containing from 1 to 4 carbon atoms.

4. The composition according to claim 3, wherein the screening agent is benzene-1,4-[di(3-methylidene-10-camphorsulphonic)]acid.

5. The composition according to claim 1, wherein the saccharide ester of ascorbic acid is ascorbyl-2-glucoside.

6. The composition according to claim 2, wherein the saccharide ester of ascorbic acid is ascorbyl-2-glucoside.

7. The composition according to claim 3, wherein the saccharide ester of ascorbic acid is ascorbyl-2-glucoside.

8. The composition according to claim 4, wherein the saccharide ester of ascorbic acid is ascorbyl-2-glucoside.

9. The composition according to claim 1, in the form of an oil-in-water emulsion or in the form of a dispersion of lipid spherules.

10. The composition according to claim 1, wherein the saccharide ester of ascorbic acid represents from 0.05% to 20% by weight relative to the total weight of the composition.

11. The composition according claim 1, wherein the UVA screening agent represents from 0.1% to 10% by weight relative to the total weight of the composition.

12. The composition according to claim 1, which additionally contains at least one hydrophilic or lipophilic adjuvant.

13. The composition according to claim 12, wherein the at least one adjuvant is selected from gelling agents, preserving agents, fragrances, fillers, dyestuffs, and active agents other than the saccharide ester of ascorbic acid and the UVA screening agent.

14. A process for treating skin marks due to ageing comprising applying the composition of claim 1 to said skin marks.

15. A process for treating wrinkles and/or fine lines on the skin comprising applying the composition of claim 1 to said wrinkles and/or fine lines.

16. A process for toning, moisturizing and/or firming up the skin comprising applying the composition of claim 1 to the skin.

17. A process for preparing a cream intended for treatment of skin diseases which leave marks on the skin comprising blending the composition of claim 1 with a cream base.

18. A process for the cosmetic or dermatological treatment of the skin, comprising applying the composition of claim 1 to the skin.

19. A process for the cosmetic or dermatological treatment of the skin, comprising applying the composition of claim 4 to the skin.

20. A process for the cosmetic or dermatological treatment of the skin, comprising applying the composition of claim 8 to the skin.

* * * * *